United States Patent [19]
Gschneidner et al.

[11] Patent Number: 5,962,710
[45] Date of Patent: Oct. 5, 1999

[54] METHOD OF PREPARING SALICYLOYLAMINO ACIDS

[75] Inventors: David Gschneidner, Stamford, Conn.; Doris O'Toole, Carmel; John Freeman, Valhalla, both of N.Y.

[73] Assignee: Emisphere Technologies, Inc., Tarrytown, N.Y.

[21] Appl. No.: 08/853,752

[22] Filed: May 9, 1997

[51] Int. Cl.⁶ .............................................. C07C 229/00
[52] U.S. Cl. ........................ 554/112; 554/109; 562/455
[58] Field of Search ............................... 554/109, 112; 562/455

[56] References Cited

U.S. PATENT DOCUMENTS

| | | |
|---|---|---|
| Re. 24,899 | 11/1960 | Green . |
| 2,671,451 | 3/1954 | Bolger ..................................... 128/260 |
| 2,828,206 | 3/1958 | Rosenberg .................................... 99/2 |
| 2,862,918 | 12/1958 | Meyer et al. ......................... 260/123.5 |
| 2,868,740 | 1/1959 | Luce ........................................... 260/8 |
| 2,971,916 | 2/1961 | Schleicher et al. ..................... 252/62.5 |
| 3,016,308 | 1/1962 | Macaulay ................................... 177/37 |
| 3,052,655 | 9/1962 | Fox et al. ................................... 260/78 |
| 3,057,344 | 10/1962 | Abella et al. ............................... 128/2 |
| 3,076,790 | 2/1963 | Fox et al. ................................... 260/78 |
| 3,170,802 | 2/1965 | Fukushima ................................ 99/145 |
| 3,190,837 | 6/1965 | Brynko et al. ........................... 252/316 |
| 3,474,777 | 10/1969 | Figge et al. ................................. 128/2 |
| 3,491,093 | 1/1970 | Pachter et al. ......................... 260/247.5 |
| 3,565,559 | 2/1971 | Sato ......................................... 424/37 |
| 3,567,650 | 3/1971 | Bakan ..................................... 252/316 |
| 3,574,832 | 4/1971 | Engel et al. ............................. 424/183 |
| 3,576,758 | 4/1971 | Emrick .................................... 252/316 |
| 3,687,926 | 8/1972 | Arima et al. .......................... 260/112.5 |
| 3,725,113 | 4/1973 | Chang ...................................... 117/82 |
| 3,748,277 | 7/1973 | Wagner .................................... 252/316 |
| 3,794,561 | 2/1974 | Matsukawa et al. ................. 195/29 R |
| 3,795,739 | 3/1974 | Birkmayer et al. ..................... 424/274 |
| 3,816,404 | 6/1974 | Kablaoui et al. ..................... 260/239.3 |
| 3,822,348 | 7/1974 | Higashi et al. ........................... 424/95 |
| 3,849,550 | 11/1974 | Teitelbaum .............................. 424/78 |
| 3,933,873 | 1/1976 | Love et al. ........................... 260/239.3 |
| 3,937,668 | 2/1976 | Zolle ....................................... 252/316 |
| 3,939,253 | 2/1976 | Bodor et al. ............................ 424/309 |
| 3,956,172 | 5/1976 | Saeki et al. ............................. 252/316 |
| 3,962,416 | 6/1976 | Katzen ...................................... 424/19 |
| 3,976,773 | 8/1976 | Curran .................................... 424/250 |
| 4,035,507 | 7/1977 | Bodor et al. ............................ 424/311 |
| 4,048,268 | 9/1977 | Ludwig ..................................... 264/15 |
| 4,061,466 | 12/1977 | Sjoholm et al. ....................... 23/230 B |
| 4,117,801 | 10/1978 | Dannelly et al. ........................ 118/20 |
| 4,147,767 | 4/1979 | Yapel ....................................... 424/22 |
| 4,183,849 | 1/1980 | Hansen ................................. 260/112.7 |
| 4,199,561 | 4/1980 | Roth et al. ................................ 424/32 |
| 4,217,370 | 8/1980 | Rawlings et al. ......................... 426/98 |
| 4,238,506 | 12/1980 | Stach et al. ............................. 424/319 |
| 4,239,635 | 12/1980 | Rieder ...................................... 252/34 |
| 4,239,754 | 12/1980 | Sache et al. ............................ 424/183 |
| 4,272,506 | 6/1981 | Schwarzberg ............................. 424/8 |
| 4,289,759 | 9/1981 | Heavner et al. ........................ 424/177 |
| 4,345,588 | 8/1982 | Widder et al. ........................... 128/1.3 |
| 4,348,384 | 9/1982 | Horikoshi et al. ...................... 424/101 |
| 4,351,337 | 9/1982 | Sidman .................................... 128/260 |
| 4,352,883 | 10/1982 | Lim .......................................... 435/178 |
| 4,357,259 | 11/1982 | Senyei et al. ............................ 252/316 |
| 4,388,304 | 6/1983 | Nyeki et al. ............................. 424/177 |
| 4,393,192 | 7/1983 | Curatolo et al. ......................... 528/292 |
| 4,402,856 | 9/1983 | Schnoring et al. ................. 428/402.22 |

(List continued on next page.)

FOREIGN PATENT DOCUMENTS

| | | | |
|---|---|---|---|
| 1077842 | 8/1976 | Canada ............................ A61K 9/50 |
| 0 000 667 A1 | 2/1979 | European Pat. Off. ......... A61K 9/50 |
| 0 036 145 A1 | 9/1981 | European Pat. Off. ....... A61K 31/62 |
| 0 068 314 | 1/1983 | European Pat. Off. ....... A61K 31/16 |
| 0 105 804 | 4/1984 | European Pat. Off. ........ C12N 15/00 |
| 0 130 162 A2 | 1/1985 | European Pat. Off. ......... B01J 13/02 |
| 0 342 054 A2 | 11/1989 | European Pat. Off. ......... A61K 7/06 |
| 0 342 056 A2 | 11/1989 | European Pat. Off. ......... A61K 7/06 |
| 0 365 183 | 4/1990 | European Pat. Off. ....... A61K 31/18 |
| 0 366 277 | 5/1990 | European Pat. Off. ....... A61K 9/107 |
| 0 418 642 | 3/1991 | European Pat. Off. ....... A61K 37/30 |
| 0 448 057 | 9/1991 | European Pat. Off. ........ C12P 21/08 |
| 0 452 161 | 10/1991 | European Pat. Off. ......... A61K 7/48 |
| 0 459 795 | 12/1991 | European Pat. Off. ....... A61K 37/02 |
| 0 467 389 | 1/1992 | European Pat. Off. ......... A61K 9/52 |
| 0 490 549 A1 | 6/1992 | European Pat. Off. ....... A61K 47/12 |
| 0 517 211 A1 | 9/1992 | European Pat. Off. ....... A61K 47/12 |
| 0 616 799 A1 | 9/1994 | European Pat. Off. ......... A61K 7/00 |
| 2 343 037 | 3/1975 | Germany . |
| 3 612 102.9 | 10/1986 | Germany ........................ C07K 15/00 |
| 71258/2 | 12/1987 | Israel . |
| 56-68612 | 6/1981 | Japan .............................. A61K 31/19 |
| 58-35111 | 3/1983 | Japan .............................. A61K 9/66 |

(List continued on next page.)

OTHER PUBLICATIONS

Airaudo, C.B. et al. (1987) *Journal of Food Science*, vol. 52(6), pp. 1750–1752.

Andini, S. et al. (1975) *Origins of Life*, vol. 6, pp. 147–153.

Brooke, S. 1 et al. (1977) *BioSystems*, vol. 9, pp. 1–22.

Chen et al. (1975) "Evidence for Hemiacetal Formation", *Biochemistry*, vol. 18, No. 5, pp. 921–925.

Davis et al. (1983) "Leucinal Inhibits . . . ", *Pharmacology Biochemistry Behavior*, vol. 19, pp. 791–794.

Dose, K. (1974) *Origins of Life*, vol. 5, pp. 239–252.

Fasman et al. (1964) *Biochemistry*, vol. 3, No. 11, pp. 1665–1674.

Fox, S.W. et al. (1976) *BioSystems*, vol. 8, pp. 40–44.

Fox, S.W. et al., *Molecular Evolution and the Origin of Life*, Maxel Decker, New York (1977).

Fox S.W. et al. (1968) *Biochim. Biophys. Acta*, vol. 160, pp. 246–249.

Fox, S.W. (1976) *Origins of Life*, vol. 7, pp. 49–68.

(List continued on next page.)

Primary Examiner—Gary Geist
Assistant Examiner—Brian J. Davis
Attorney, Agent, or Firm—Darby & Darby

[57] ABSTRACT

A method for preparing salicyloylamino acids is provided. An oligosalicylate and an amino acid are reacted to yield the salicyloylamino acid.

21 Claims, No Drawings

U.S. PATENT DOCUMENTS

| | | | |
|---|---|---|---|
| 4,402,968 | 9/1983 | Martin | 424/273 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,457,907 | 7/1984 | Porter | 424/7.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,683,092 | 7/1987 | Tsang | 264/4.3 |
| 4,690,786 | 9/1987 | Ninomiya et al. | 264/4.6 |
| 4,692,284 | 9/1987 | Braden | 264/4.3 |
| 4,692,433 | 9/1987 | Hostetler et al. | 514/12 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,908,233 | 3/1990 | Takizawa et al. | 427/213.35 |
| 4,919,939 | 4/1990 | Baker | 424/493 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. | 424/497 |
| 5,023,374 | 6/1991 | Simon | 564/152 |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. | 424/401 |
| 5,271,961 | 12/1993 | Mathiowitz et al. | 427/213.31 |
| 5,278,148 | 1/1994 | Branca et al. | 514/19 |
| 5,310,535 | 5/1994 | Kruper, Jr. et al. | 424/1.53 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,377 | 2/1995 | Chagnon et al. | 424/450 |
| 5,389,379 | 2/1995 | Dirix et al. | 424/451 |
| 5,401,516 | 3/1995 | Milstein et al. | 424/491 |
| 5,418,010 | 5/1995 | Janda et al. | 427/213.31 |
| 5,439,686 | 8/1995 | Desai et al. | 424/451 |
| 5,443,841 | 8/1995 | Milstein et al. | 424/451 |
| 5,447,728 | 9/1995 | Milstein et al. | 424/490 |
| 5,451,410 | 9/1995 | Milstein et al. | 424/490 |
| 5,474,997 | 12/1995 | Gray et al. | 514/252 |
| 5,536,813 | 7/1996 | Charpenel et al. | 530/324 |
| 5,540,939 | 7/1996 | Milstein et al. | 424/491 |
| 5,541,155 | 7/1996 | Leone-Bay et al. | 514/2 |
| 5,578,323 | 11/1996 | Milstein et al. | 424/499 |
| 5,601,846 | 2/1997 | Milstein et al. | 424/499 |
| 5,629,020 | 5/1997 | Leone-Bay et al. | 424/489 |
| 5,643,957 | 7/1997 | Leone-Bay et al. | 514/563 |
| 5,650,386 | 7/1997 | Leone-Bay et al. | 514/2 |
| 5,665,700 | 9/1997 | Cho et al. | 514/2 |
| 5,667,806 | 9/1997 | Kantor | 424/484 |
| 5,693,338 | 12/1997 | Milstein . | |
| 5,705,529 | 1/1998 | Matyus et al. . | |
| 5,709,861 | 1/1998 | Santiago et al. . | |
| 5,714,167 | 2/1998 | Milstein et al. . | |
| 5,750,147 | 5/1998 | Kantor . | |

FOREIGN PATENT DOCUMENTS

| | | | |
|---|---|---|---|
| 6-107682 | 4/1994 | Japan . | |
| 929401 | 6/1963 | United Kingdom . | |
| 1 075 952 | 8/1967 | United Kingdom . | |
| 1 236 885 | 6/1971 | United Kingdom . | |
| 1 567 763 | 5/1980 | United Kingdom | A61K 9/22 |
| 2 095 994 | 10/1982 | United Kingdom | A61K 9/00 |
| WO 85/00110 | 1/1985 | WIPO | A61K 47/00 |
| Wo 85/00105 | 1/1985 | WIPO | A61K 9/52 |
| WO 85/00809 | 2/1985 | WIPO | C07D 233/64 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |
| WO 93/25583 | 12/1993 | WIPO | C07K 15/00 |
| WO 94/11015 | 5/1994 | WIPO | A61K 37/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |
| WO 85/02772 | 7/1995 | WIPO | A61K 49/00 |
| WO 95/28838 | 11/1995 | WIPO | A01N 37/46 |
| WO 95/28920 | 11/1995 | WIPO | A61K 31/19 |
| WO 96/12473 | 5/1996 | WIPO | A61K 9/16 |
| WO 96/12474 | 5/1996 | WIPO | A61K 9/16 |
| WO 96/12475 | 5/1996 | WIPO | A61K 9/16 |
| WO 96/21464 | 7/1996 | WIPO | A61K 39/00 |
| WO 96/30036 | 10/1996 | WIPO | A61K 38/00 |
| WO 96/33699 | 10/1996 | WIPO | A61K 9/16 |
| WO 96/39835 | 12/1996 | WIPO | A01N 43/50 |
| WO 96/40070 | 12/1996 | WIPO | A61K 9/14 |
| WO 96/40076 | 12/1996 | WIPO | A61K 9/16 |
| WO 97/10197 | 3/1997 | WIPO | C01C 51/10 |
| WO 97/31938 | 9/1997 | WIPO | C07K 5/00 |
| WO 97/364480 | 10/1997 | WIPO | A01N 37/12 |
| WO 97/47288 | 12/1997 | WIPO . | |

OTHER PUBLICATIONS

Fox S.W. (1980) *Naturwissenschaften,* vol. 67, pp. 378–383.
Fox, S.W. et al. (1960) *Archives of Biochemistry and Biophysics,* vol. 86, pp. 281–285.
Fox, S.W. et al. (1974) *Origins of Life,* vol. 5, pp. 227–237.
Fox, S.W. (1984) *Origins of Life,* vol. 14, pp. 485–488.
Gol'dovskii, A.M. (1978) *Zhurnal Evolyutsionnoi Biokhimii i Fiziologii,* vol. 14(6), pp. 437–439.
Gurrieri, S. et al. (1973) *Thermochimica Acta,* vol. 7, pp. 231–239.
Harada, K. et al (1979) *BioSystems,* vol. 11, pp. 47–53.
Harada et al., (1960) *Archives of Biochemistry and Biophysics,* vol. 86, pp. 274–280.
Hare (1970) *Etude Cenetique De La Polycondensation Thermique D'$_x$–Amino Acides,* vol. 45, pp. 330–339.
Heinrich, M.R. et al. (1969) *Archives of Biochemistry and Biophysics,* vol. 130, pp. 441–448.
Heinz, B. et al. (1981) *BioSystems,* vol. 14, pp. 33–40.
Hennon, G. et al. (1975) *Biochimie,* vol. 57, pp. 1395–1396.
Hsu, L.L. et al. (1976) *BioSystems,* vol. 8, pp. 89–101.
Hsu, L.L. et al. (1971) *Currents in Modern Biology,* vol. 4, pp. 12–25.
Ishima, Y. et al. (1981), *BioSystems,* vol.14, pp. 243–251.
Jackson et al. (1991) "Pharmacological . . . ", *J. Pharm. & Exp. Thera.,* vol. 261, No. 1, pp. 546–552.
Jungck, J.R. et al. (1973) *Naturwissenschaften,* vol. 60, pp. 425–427.
Kokufuta, E. et al. (1984) *BioSystems,* vol. 16, pp. 175–181.
Lacey, Jr., J.C. et al. (1979) *BioSystems,* vol. 11, pp. 9–17.
Lacey, Jr., J.C. et al. (1979) *BioSystems,* vol. 11, pp. 1–7.
Martinez Luque–Romero, M. et al. (1986) *BioSystems,* vol. 19, pp. 267–272.
Masinovsky, Z. et al (1989) *BioSystems,* vol. 22, pp. 305–310.
Matsuno, K. (1982) *BioSystems,* vol. 15, pp. 1–11.
Matsuno, K. (1984) *BioSystems,* vol. 17, pp. 11–14.
Matsuno, K. (1981) *BioSystems,* vol. 14, pp. 163–170.
McAlhaney, W.W. et al. (1976) *BioSystems,* vol. 8, pp. 45–50.
Melius, P. et al. (1987) *BioSystems,* vol. 20, pp. 213–217.
Melius, P. et al. (1975) *Bioorganic Chemistry,* vol. 4, pp. 385–391.
Melius, P. (1979) *BioSystems,* vol. 11, pp. 125–132.
Miquel, J. et al. (1971) *Currents in Modern Biology,* vol. 3, pp. 299–306.
Nakashima, T. et al. (1980) *J. Mol. Evol.,* vol. 15, pp. 161–168.
Nakashima, T. et al. (1981) *BioSystems,* vol. 14, pp. 151–161.
Novak, V.J.A. (1984) *Origins of Life,* vol. 14, pp. 513–522.
Olafsson, P.G. et al. (1971) *Polymer Letters,* vol. 9, pp. 521–528.
Phillips, R.D. et al. (1974) *Int. J. Peptide Protein Res.,* vol. 6, pp. 309–319.
Przybylski, A.T. et al. (1982) *Die Naturwissenschaften,* vol. 69, pp. 561–563.
Przybylski, A.T. et al. (1984) *Applied Biochemistry and Biotechnology,* vol. 10, pp. 301–307.
Przybylski, A.T. (1985) *BioSystems,* vol. 17, pp. 218–288.
Rohlfing, D.L. (1975) *Origins of Life,* vol. 6, pp. 203–209.
Rohlfing, D.L. (1970) *Science,* vol. 169, pp. 998–1000.
Rohlfing, D.L. (1967) *Archives of Biochemistry and Biophysics,* vol. 118, pp. 468–474.
Rohlfing, D.L. et al. *Catalytic Activities of Thermal Polyanhydro–α–Amino Acids,* pp. 373–418, 1969.
Rohlfing, D.L. et al. (1976) *BioSystems,* vol. 8, pp. 139–145.
Ryan, J.W. et al. (1973) *BioSystems,* vol. 5, pp. 115–118.
Saunders, M.A. et al. (1974) *BioSystems,* vol. 6, pp. 81–92.
Snyder, W.D. et al. (1975) *BioSystems,* vol. 7, pp. 222–229.
Sokol, P.E. (1974) *Journal of the American Oil Chemists'Society,* vol. 52, pp. 101–102.
Vaughan, G. et al. (1987) *BioSystems,* vol. 20, pp. 219–223.
Vol'kenshtein, M.V. (1989) *Molekulyarnaya Biologiya,* vol. 23(1), pp. 23–37.
Waehneldt, T.V. et al. (1968) *Biochim. Biophys. Acta,* vol. 160, pp. 239–245.
Williams et al. (1991) *J. Biol. Chem.,* vol. 266, No. 8, pp. 5182–5190.
Yuki, A. et al. (1969) *Biochemical and Biophysical Research Communications,* vol. 36(4), pp. 657–663.
Zulaski et al. (1983) "New Carboxyalkyl Inhibitors of Brain Enkenphalinase", *J. Med. Chem.,* 26, pp. 60–65.
(1985) *Chemical Abstracts,* vol. No. 105(1), Abstract No. 12027p.
(1985) *Chemical Abstracts,* vol. No. 102(6), Abstract No. 50870d.
*Chemical Abstract,* vol. 80(9) Abst. No. 52392a.
Bergeron, Raymond J., et al. (1994) "Macromolecular Self–sof Diketopiperazine Tetrapeptides", *Journal of the American Chemical Society,* vol. 116, pp. 8479–8484.
Bergeron, Raymond J., et al. (1993) "A Comparative Study of the Iron–Cleaning Properties of Desferrithiocin Analogues With Desferrioxamine B in a Cebus Monkey Model", *Blood,* vol. 81, No. 8, pp. 2166–2173.
Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood,* vol. 79, No. 7, pp. 1882–1890.
Bergeron, Raymond J., et al. (1991) "Evaluation of Desferrithiocin and Its Synthetic Analogs as Orally Effective Iron Chelators", *Journal of Medicinal Chemistry,* vol. 34, No. 7, pp. 2072–2078.
Bergeron, Raymond et al., "A Comparative Evaluation of Iron Clearance Models", *Annals New York Academy of Sciences,* pp. 278–393, Mar. 13–15, 1990.
Andriuoli, G., et al. (1990), *Haemostasis* 20 (suppl. 1):154–158.
Caramazza, I., et al. (1991), *Thrombosis Research* 62:785–789.
Guarini, S., et al. (1983), *Experimentia* 41:350–352.
Guarini, S., et al. (1985), *Pharmacological Research Communications* 17(8):685–697.
Dal Pozzo, A., et al. (1989), *Thrombosis Research* 56:119–124.
Gelb, R., et al (1983), *Lite Sciences* 33(1):83–85.
Watterberg et al. (1988), *Pediatric Research,* vol. 23, No. 4, part 2, p. 570A, column 1, abstract No. 2209.
Berstein (1985), *Chest* 87(1):68S–73S.
Damge et al. (1988), *Diabetes* 37:246–251.
*Chemical Abstracts*:83 18436Ok, (1975).
Amino, Y., et al., *Chem. Pharm. Bull.* 36(11):4426–4434 (1988).
Baughman, R.A. et al., *Proc. of the 6th Inter'l. Symp. on Recent Advs. in Drug Delivery Systems, Ctr. for Controlled Chem. Delivery, University of Utah,* Feb. 22–25, 1993, Salt Lake City, UT, pp. 179–180 "Methods for Assessing The Stability of Proteinoid Microspheres".
Haas, S. et al., "Assessment Of Stability Of Proteinoid Microspheres", *Proceed. Intern. Symp. Control. Rel. Bioact. Mater.,* 20 (1993), Controlled Release Society, Inc.
X. Ma, et al., *Proceed. Intern. Symp. Control. Rel. Bioact. Mater.,* 20 (1993), Controlled Release Society, Inc. "In Vitro Mechanistic Investigation of the Proteinoid Microsphere Oral Delivery System".

Yen, H.-R H., et al., "Adsorption of Sulforhodamine 101 on Proteinoid Microspheres" *Proceed. Intern. Symp. Control. Rel. Bioact. Mater.,* 20 (1993), Controlled Release Society, Inc.

Presented at "IBC Rational Drug Design Conference", San Diego, Calif. — Dec. 1994.

Leone–Bay et al., Presented at *"Winter Conference on Medicinal and Bioorganic Chemistry"* Steamboat Springs, Colorado — Feb. 1995 "Microsphere Formation and Drug Delivery in a Series of Derivatized Amino Acids".

Santiago et al., *Pharm. Res.* 11: 1994, p.S–298 "Oral Delivery of Heparin Microspheres made with Modified Amino Acids".

Leone–Bay et al., *Pharm. Res.* 11: 1994, p.S–121 "Oral Delivery of Heparin using Acylated Amino Acids".

Sarubbi et al., *Pharm. Res.* 11: 1994, p.S–299 "Oral Calcitonin Delivery using the PODDS Technology".

Leipold et al., *Pharm. Res.* 11 1994, p.S–298 "Oral Delivery of Interferon in Rats and Primates".

Santiago et al., *Pharm. Res.* 11: 1994, p.S–298 "Evaluation in Rats of Vehicles for the Oral Delivery of Low Molecular Weight Heparin".

X. Ma et al., PPD 7303 *Pharmaceutical Research* 9(10):S–244, 1992 (Oct. Supplement).

Milstein et al., *Symposia Abstracts.* AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.,* 20 (1993), Controlled Release Society, Inc.

Santiago et al. "Oral Immunization of Rats with Influenza Virus M Protein (M1) Microspheres" *Proceed. Inter. Symp. Control. Rel. Bioact. Mater.,* 19 (1992), Controlled Release Society, Inc., pp. 116–117.

Santiago et al. "Proteinoid Microspheres For The Oral Delivery of Heparin" *Proceed. Intern. Symp. Control. Rel. Bioact. Mater.,* 19 (1992), Controlled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.,* 19 (1992), Controlled Release Society, Inc. pp. 516–517.

Doris K. Chiappetta, *Eastern Analytical Symposium,* Nov 17, 1992 "Solutions for Problems in Bioanalysis".

Elizabeth A. Harris. M.S., *Eastern Analytical Symposium,* Nov. 17, 1992 "Solutions for Problems in Bioanalysis".

AAPS 6TH Ann. Meeting and Expo., "Proteinoids — A Novel Drug Delivery System" Nov. 19, 1992, p.33.

Milstein et al., "Efficient Oral Delivery Of Monoclonal Antibodies By Proteinoid Encapsulation" *The 1993 Miami Bio/Technology Winter Symposium — Advances in Gene Technology: Protein Engineering and Beyond,* Jan. 17–22, 1993.

Xinghang Ma, et al. "Stability Study of Drug–loaded Proteinoid Microsphere Formulations during Freeze–drying" *Journal of Drug Targeting,* 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems,* Ctr. for Controlled Chem. Delivery, University of Utah, Feb. 22–25, 1993, pp. 181–182.

Robert O. Dillman, M.D., *Annals of Internal Medicine* 1989:111 pp. 592–600, "Monoclonal Antibodies for Treating Cancer".

Brendan D. Curti, *Critical Reviews in Oncology/Hematology,* 1993: 14 pp. 29–39 "Physical barriers to drug delivery in tumors".

V. Hird et al, *Genes and Cancer,* edited by Desmond Carney & Karol Sikora, pp.183–189, Immunotherapy with Monoclonal Antibodies.

Michael E. Osband et al., *Immunology Today,* vol. 11, No.6 1990, pp. 193–195, "Problems in the investigational study and clinical use of cancer immunotherapy".

William J. Harris, *Tibtech* Feb. 1993 vol.11, pp. 42–44 "Therapeutic antibodies — the coming of age".

Thomas A. Waldmann, *Science,* Jun. 21, 1991, 252:1657–1662, "Monoclonal Antibodies in Diagnosis and Therapy".

*Chemical Abstracts,* 76(14):72994u, (1971).

*Chemical Abstracts,* 84(7):44660d, (1975).

*Chemical Abstracts,* 86(16):107529g, (1976).

*Chemical Abstracts,* 112(15):134663h, (1989).

*Chemical Abstracts,* 114(22):214519x, (1990).

J. Györe et al., *Thermal Analysis,* vol. 2 — Proceeding Fourth ICTA Budapest 1974, pp.387–394.

*Chemical Abstracts,* 99(19) 158832b, (1982).

*Derwent Abstracts,* JP 67008622, (1967).

*Journal of Medicinal Chemistry,* vol. 38, No. 21, pp. 4257–4262, (1995), "Microsphere Formation in a Series of Derivatized α–Amino Acids: Properties, Molecular Modeling, and Oral Delivery of Salmon Calcitonin".

Andrea Leone–Bay et al., *Journal of Medicinal Chemistry,* vol. 38, No. 21, pp.4263–4269, (1995), "N–Acylated α–Amino Acids as Novel Oral Delivery Agents for Proteins".

*The Extra Pharmacopoeia,* Thirtieth Edition, pp. 325–326, (1993).

Stephen J. Douglas et al., *Chemistry and Industry,* vol. 22:748–751, 1985.

C.A. Finch, *Chemistry and Industry,* vol. 22:752–756, 1985.

John A. Butera et al., *J. Med. Chem.,* vol. 34:3212–3228, 1990.

Madeline G. Cimini et al., *Ann. Report in Med. Chem.,* vol. 27:89–98., 1992.

Bernadette Earley et al., *Brain Research,* vol. 546:282–286, 1991.

John W. Ellingboe et al., *J. Med. Chem.,* vol. 35:705–716, 1992.

William C. Lumma et al., *J. Med. Chem.,* vol. 30:758–763, 1987.

Joseph J. Lynch et al., *J. of Pharm. and Exp. Therap.,* vol. 269:541–554, 1994.

Kiyoshi Matsuno et al., *Brain Research,* vol. 575:315–319, 1992.

Thomas K. Morgan et al., *J. Med. Chem.,* vol. 33:1091–1097, 1990.

Hitoshi Oinuma et al., *J. Med Chem.,* vol. 33:903–905, 1990.

Tadimeti S. Rao et al., *Molecular Pharmacology,* vol.37:978–982, 1990.

Asaji Kondo, *Microcapsule Processing and Technology,* pp. 154–165, 1979.

G. Pastores et al., *J. Liquid Chromatography,* 18(15):3049–3059, 1995.

D. Sinha et al., *J. Bio. Chem.,* 260(19):10714–10719. 1985.

E. Franssen et al., *J. Med. Chem.,* 35:1246–1259, 1992.

*Chemical Abstracts,* 99(23):191473h, Dec. 5, 1983.

R. Langer, *Science,* 249:1528, Sep. 28, 1990.

M. Alonso et al., *Vaccine,* 12:299, 1994.

A. Leone–Bay et al., *J. Med. Chem.,* 39:2571–2578, 1996.

R. Thompson, *Biochemistry,* 12:47–51, 1973.

S. Thompson, *J. Med. Chem.,* abstract, 86:174780, 1986.

METHOD OF PREPARING SALICYLOYLAMINO ACIDS

FIELD OF THE INVENTION

The present invention relates to methods for preparing salicyloylamino acids. Certain salicyloylamino acids are useful in the delivery of active agents, such as for example, biologically or chemically active agents, to a target.

BACKGROUND OF THE INVENTION

Certain salicyloylamino acids have been demonstrated as being useful in the delivery of active agents, particularly, through the oral route. See, for example, U.S. patent application Ser. No. 08/414,654, now U.S. Pat. No. 5,650,386, filed Mar. 31, 1995, now U.S. Pat. No. 5,650,386.

Two methods of preparation of such compounds are illustrated in U.S. patent application Ser. No. 08/414,654, now U.S. Pat. No. 5,650,386, filed Mar. 31, 1995 and provisional U.S. patent application Ser. No. 60/003,111, filed Sep. 1, 1995, published as WO96/30036, Oct. 3, 1996.

Additionally, Ho et al., Synthetic Communications, 26(14), 2641–2649 (1986) summarizes a number of methods for the preparation of ω-aminoalkanoic acids. These methods include the introduction of an amine group by the conversion of a ketone to an oxime or a carboxylate to a nitrile, followed by reduction by azidide opening of an anhydride, followed by Schmidt rearrangement, or by Hoffman rearrangement of an amide with aqueous base and bromine. Boc protected and N-acylated ω-amino alkanoic acids can also be obtained by hydrolysis of the N-Boc and N-acylated lactams, respectively. Ho et al. presents an additional synthetic route to N-Boc protected or Boc-amino acid coupled with ω-aminoalkanoic acids.

However, there is still a need for an efficient, economical, and commercially practical method for the preparation of salicyloylamino acids.

SUMMARY OF THE INVENTION

A method for preparing a salicyloyl amino acid is provided in which an oligosalicylate and an amino acid are reacted to yield the salicyloyl amino acid.

DETAILED DESCRIPTION OF THE INVENTION

Oligosalicylates are typically represented by the formula

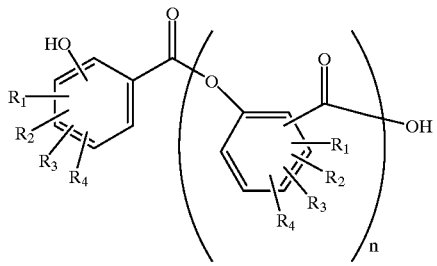

wherein $R_1$, $R_2$, $R_3$ and $R_4$ are independently hydrogen, fluorine, chlorine, bromine, iodine, $C_{1-9}$ linear or branched chain alkyl, $C_{1-9}$ linear or branched chain alkoxy, $C_{6-14}$ aryl, $C_{6-14}$ aryloxy or ($C_{6-14}$ aryl)($C_{1-9}$ linear or branched chain alkyl); and wherein n is an integer from about 1 to about 10.

Preferred oligosalicylates are represented by the formulae

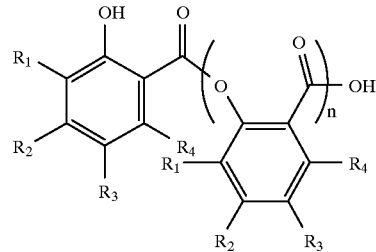

wherein $R_1$, $R_2$, $R_3$ and $R_4$ are independently hydrogen, fluorine, chlorine, bromine, iodine, $C_{1-9}$ linear or branched chain alkyl, $C_{1-9}$ linear or branched chain alkoxy, $C_{6-14}$ aryl, $C_{6-14}$ aryloxy or ($C_{6-14}$ aryl)($C_{1-9}$ linear or branched chain alkyl); and wherein n is an integer from about 1 to about 10;

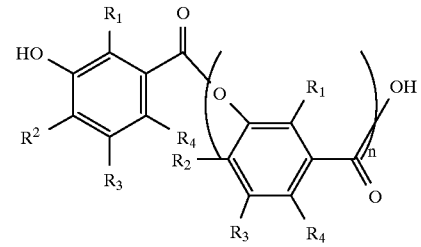

wherein $R_1$, $R_2$, $R_3$ and $R_4$ are independently hydrogen, fluorine, chlorine, bromine, iodine, $C_{1-9}$ linear or branched chain alkyl, $C_{1-9}$ linear or branched chain alkoxy, $C_{6-14}$ aryl, $C_{6-14}$ aryloxy or ($C_{6-14}$ aryl)($C_{1-9}$ linear or branched chain alkyl); and wherein n is an integer from about 1 to about 10; and

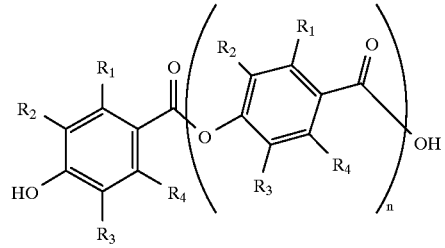

wherein $R_1$, $R_2$, $R_3$ and $R_4$ are independently hydrogen, fluorine, chlorine, bromine, iodine, $C_{1-9}$ linear or branched chain alkyl, $C_{1-9}$ linear or branched chain alkoxy, $C_{6-14}$ aryl, $C_{6-14}$ aryloxy or ($C_{6-14}$ aryl)($C_{1-9}$ linear or branched chain alkyl); and wherein n is an integer from about 1 to about 10.

Most preferred oligosalicylates are oligosalicylate, oligo-methyl salicylate, and oligo-dichlorosalicylate.

An amino acid is any carboxylic acid having at least one free amine group and includes naturally occurring and synthetic amino acids. Many amino acids and amino acid esters are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y. USA).

Representative, but not limiting, amino acids for use in the present invention are generally of the formula

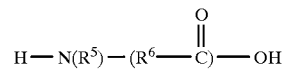

wherein:

R⁵ is hydrogen, $C_1-C_4$ alkyl, or $C_2-C_4$ alkenyl;

R⁶ is $C_1-C_{24}$ alkyl, $C_2-C_{24}$ alkenyl, $C_3-C_{10}$ cycloalkyl, phenyl, naphthyl, ($C_1-C_{10}$ alkyl) phenyl, ($C_2-C_{10}$ alkenyl) phenyl ($C_1-C_{10}$ alkyl) naphthyl, ($C_2-C_{10}$ alkenyl) naphthyl, phenyl ($C_1-C_{10}$ alkyl), phenyl ($C_2-C_{10}$ alkenyl), naphthyl ($C_1-C_{10}$ alkyl), or naphthyl ($C_2-C_{10}$ alkyl) or naphthyl ($C_2-C_{10}$ alkenyl);

R⁶ being optionally substituted with $C_1-C_4$ alkyl, $C_2-C_4$ alkyenyl, $C_1-C_4$ alkoxy, —OH, —SH, —$CO_2R^7$, $C_3-C_{10}$ cycloalkyl, $C_3-C_{10}$ cycloalkenyl, heterocycle having 3–10 ring atoms wherein the hetero atom is one or more of N, O, S, or any combination thereof, aryl, ($C_1-C_{10}$ alk)aryl, ar($C_1-C_{10}$ alkyl) or any combination thereof;

R⁶ being optionally interrupted by oxygen, nitrogen, sulfur, or any combination thereof; and R⁷ is hydrogen, $C_1-C_4$ alkyl, or $C_2-C_4$ alkenyl.

The preferred naturally occurring amino acids are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, phenylglycine, or O-phosphoserine. The preferred amino acids are arginine, leucine, lysine, phenylanine, tyrosine, tryptophan, valine, and phenylglycine.

The preferred non-naturally occurring amino acids are β-alanine, α-amino butyric acid, γ-amino butyric acid, γ-(aminophenyl) butyric acid, α-amino isobutyric acid, citrulline, ε-amino caproic acid, 7-amino heptanoic acid, β-aspartic acid, aminobenzoic acid, aminocaprylic acid, aminophenyl acetic acid, aminophenyl butyric acid, γ-glutamic acid, cysteine (ACM), ε-lysine, ε-lysine (A-Fmoc), methionine sulfone, norleucine, norvaline, ornithine, d-ornithine, p-nitro-phenylalanine, hydroxy proline, 1,2,3,4,-tetrahydroisoquinoline-3-carboxylic acid, aminodecanoic acid, and thioproline. Most preferred amino acids are aminocaprylic acid and aminodecanoic acid.

Poly amino acids are either peptides or two or more amino acids linked by a bond formed by other groups which can be linked, e.g., an ester, anhydride or an anhydride linkage. Poly amino acids can be homo- or hetero-poly amino acids, and can include natural amino acids, synthetic amino acids, or any combination thereof.

Peptides are two or more amino acids joined by a peptide bond. Peptides can vary in length from di-peptides with two amino acids to polypeptides with several hundred amino acids. See, Walker, *Chambers Biological Dictionary*, Cambridge, England: Chambers Cambridge, 1989, page 215.

The present reaction is typically conducted in an aqueous medium (which can contain sodium hydroxide) and in the presence of one or more organic solvents such as, for example, dioxane, xylenes, acetonitrile, tetrahydrofuran, and 1-methoxy-2-propanol. Preferred reaction temperatures range from about 25 degrees C. to about 150 degrees C. Preferred reaction times range from about 0.5 to about 24 hours. Typically, the molar ratio of the oligosalicylate reactant to the amino acid reactant will range from about 0.5 to about 2.0.

The reaction product can be isolated from the reaction mixture by, for example, filtration followed by drying of the filtrate.

DESCRIPTION OF THE PREFERRED EMBODIMENTS

The following Examples illustrate the invention without limitation. All parts are given by weight unless otherwise indicated.

EXAMPLE 1

Preparation of N-(salicyloyl)-8-aminocaprylic acid

A. Preparation of Cyclooctanone Oxime Hydrochloride

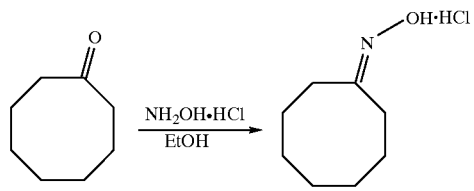

Cyclooctanone (50 g, 0.396 mol, 1.0 eq) and ethanol (250 mL) were placed in a 500 mL round bottom flask equipped with a magnetic stir bar. Hydroxylamine hydrochloride (28.91 g, 0.416 mol, 1.05 eq) was added slowly. The cloudy reaction mixture was stirred at 25 degrees C. for 20 min and heated to 50 degrees C. for 30 min, during which time it turned clear. Upon cooling to 25 degrees C., the mixture was concentrated to produce an off-white solid, which still contained a small amount of ethanol. The cyclooctanone oxime hydrochloride was used without further purification.

B. Preparation of 2-Azacyclononanone

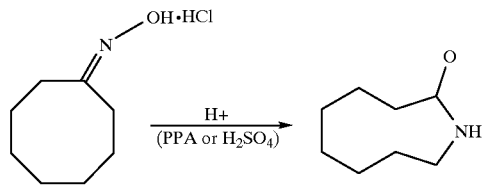

Cyclooctanone oxime hydrochloride (6.7 g., 39.6 mmol, 1.0 eq) and formic acid (15 mL) were placed in a 100 mL round bottom flask equipped with a magnetic stirrer, a cold-water condenser and a nitrogen purge. The mixture was treated with concentrated sulfuric acid (2.1 mL, 39.6 mmol, 1.0 eq) and heated to reflux. After 3.5 hours, no starting material was observed by TLC. The now black reaction mixture was cooled to 25 degrees C. and poured slowly into 200 mL of ice water. The pH was adjusted to 7.5–8.0 with 10N NaOH. The aqueous mixture was extracted with chloroform (3 times).

The combined organic layers were dried over $Na_2SO_4$ and concentrated in vacuo. The residue was purified by Kugelrohr distillation. The 2-azacyclononanone was isolated as a colorless liquid (3.76 g, 75%).

C. Preparation of 2-Azacyclononanone

Polyphosphoric acid (31.9 g) and water (3.75 g) were placed in a 100 mL round bottom flask equipped with a stir bar and a cold water condenser. The mixture was heated to 130 degrees C., and cyclooctanone oxime hydrochloride (5.9 g, 35 mmol, 1.0 eq) was added in small portions over 10 min. The oxime dissolved readily. The reaction mixture was stirred at 130 degrees C. for 1 hour, turned dark, was cooled to 100 degrees C., and poured into 100 mL of ice water. The aqueous mixture was extracted with chloroform (3×75 mL). The combined organic layers were dried over $Na_2SO_4$ and concentrated in vacuo. The 2-azacyclononanone slowly crystallized into an off-white solid (4.69 g, 94%).

D. Preparation of Oligosalicylate

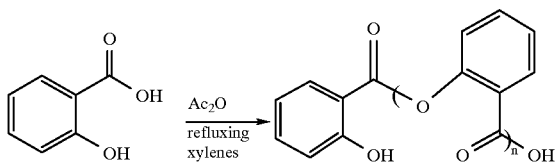

Acetic anhydride (14.50 mL, 15.69 g, 0.154 mol, 1.02 eq), salicylic acid (20.79 g, 0.151 mmol, 1.00 eq), and xylenes (60 mL) were added to a 250 mL, three-neck flask fitted with a magnetic stir bar, a thermometer, and a DeanStark trap with condenser. The flask was placed in a sand bath and heating of the cloudy white mixture was begun. The reaction mixture became a clear solution around 100 degrees C. Most of the volatile organics (xylenes and acetic acid) distilled into the Dean-Stark trap over three hours (135–146 degrees C). Distillation was continued for another hour (a total of 75 mL distilled), during which the pot temperature slowly rose to 195 degrees C. and the distillate slowed to a trickle. The residue was poured off while still hot into an aluminum tray. Upon cooling a brittle yellow glass formed. The solid was ground to a fine powder. The 18.95 g of oligosalicylate produced was used without further purification.

E. Preparation of Salicyloylamino acid

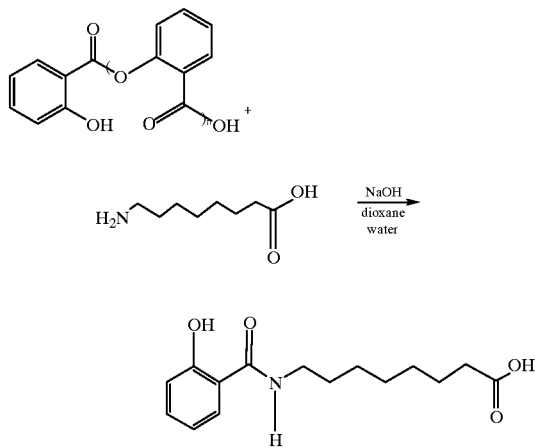

A 10N sodium hydroxide solution of (4.4 mL, 44.0 mmol, 1.18 eq), 8-aminocaprylic acid (5.93 g, 37.2 mmol, 1.00 eq), sodium bicarbonate (0.88 g, 10.4 mmol, 0.28 eq) and water (5 mL) were added to a 250 mL round bottom flask equipped with a magnetic stir bar and an addition funnel. The white cloudy mixture was treated with a solution of oligosalicylate (5.20 g, 42.9 mmol 1.15 eq) and dioxane (20 mL), added over five minutes. The addition funnel was replaced with a condenser, and the reaction mixture was heated to 90 degrees C. for 3 hours (at which time the reaction was determined to have finished, by HPLC). The clear orange reaction mixture was cooled to 40 degrees C., filtered and acidified to pH=1 with 3% (by vol.) aqueous hydrochloric acid. All of the dioxane and some of the water were stripped (60 degrees C., 50 mm). The solid (which precipitated from solution during stripping) was isolated by filtration while still warm. The light pink solid was recrystallized from 50 mL of 65% ethanol-water. The solid was recovered by filtration and was dried over 18 hours in a 50 degrees C. vacuum oven. The N-(salicyloyl)-8-aminocaprylic acid was isolated as a white solid (5.35 g, 51%).

F. Preparation of Salicyloylamino acid

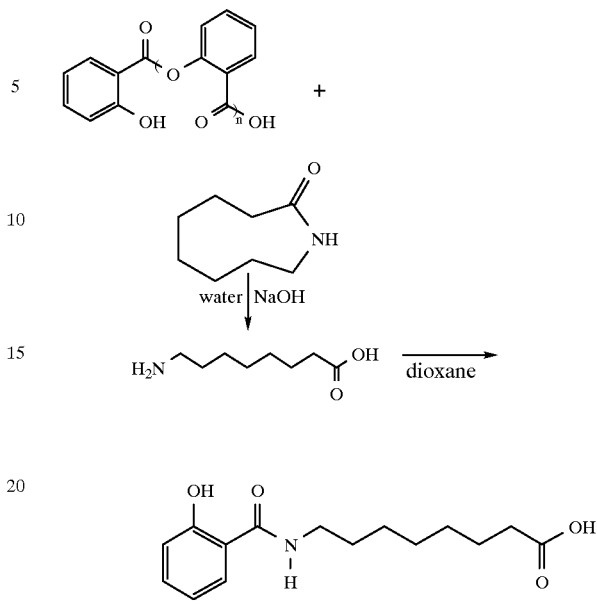

Sodium hydroxide (1.68 g, 42.0 mmol, 1.2 eq), 2-azacyclononanone (5.0 g, 35.5 mmol, 1.0 eq) and 20 mL of water were placed a 100 mL round bottom flask equipped with a magnetic stir bar and cold water condenser to prepare aminocaprylic acid. The reaction mixture was heated to reflux for 2.5 hours (at which time the reaction was determined to have finished, by TLC) and cooled to 25 degrees C. A solution of oligosalicylate (4.87 g, 40 mmol, 1.1 eq) and dioxane (50 mL) was added to the aqueous solution of 8-aminocaprylic acid. This mixture was heated to reflux for 2.25 hours (at which time the reaction was determined to have finished, by HPLC). The clear orange reaction mixture was cooled to 25 degrees C. and acidified to pH=1 with 3% (by vol.) aqueous hydrochloric acid. All the dioxane and some of the water were stripped (60 degrees C., 50 min). The aqueous phase was decanted from the brown oil while still warm. Crystallization of the oil from ethanol-water yielded a white precipitate. The solid was recovered by filtration and was dried over 4 hours in a 50 degrees C. vacuum oven. The N-(salicyloyl)-8-aminocaprylic acid was isolated as a white solid (5.73 g, 59%).

EXAMPLE 2

Preparation of Oligo(3-methylsalicylate)

A. Preparation of Oligo N-(3-methylsalicyloyl)-8-aminocaprylic Acid

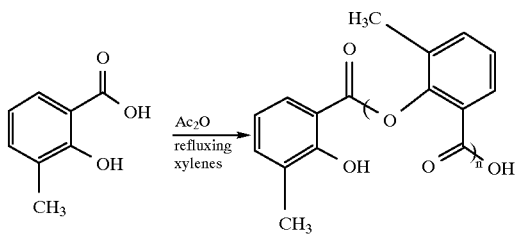

Acetic anhydride (11.10 mL, 12.01 g, 0.118 mol, 1.03 eq), 3-methylsalicylic acid (17.37 g, 0.114 mmol, 1.00 eq), and xylenes (60 mL) were added to a 250 mL, three-neck flask fitted with a magnetic stir bar, a thermometer, and a Dean-Stark trap with condenser. The flask was placed in a sand bath and heating of the cloudy white mixture was begun. The reaction mixture cleared to a yellow solution around 100 degrees C. Most of the volatile organics (xylenes and acetic acid) were distilled into the Dean-Stark trap over three hours (135–146 degrees C.). Distillation was continued for another hour (a total of 75 mL distilled), during which the pot temperature slowly rose to 175 degrees C. and the distillate slowed to a trickle. The residue was poured off while still hot into an aluminum tray. Upon cooling a brittle yellow glass formed. The solid was ground to a fine powder. The 15.90 g of oligo(3-methylsalicylate) produced was used without further purification.

B. Preparation of Salicyloylamino acid

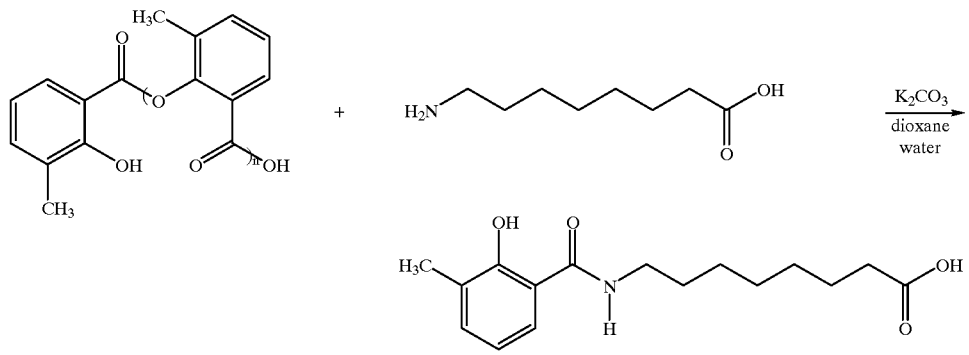

A 50% (by weight) solution of potassium carbonate (24 mL, 36 g, 0.127 mol, 1.23 eq), 8-aminocaprylic acid (16.44 g, 0.103 mol, 1.00 eq), and water (20 mL) were added to a 250 mL round bottom flask equipped with a magnetic stir bar and an addition funnel. The white cloudy mixture was treated with a solution of oligo(3-methylsalicylate) (15.90 g, 0.114 mmol 1.11 eq) and dioxane (90 mL), added over five minutes. The addition funnel was replaced with a condenser, and the reaction mixture was heated to 90 degrees C. for 4 hours (at which time the reaction was determined to have finished, by HPLC). The clear orange reaction mixture was cooled to 40 degrees C. and acidified to pH=1 with 3% (by vol.) aqueous hydrochloric acid. All the dioxane and some of the water were stripped (60 degrees C., 50 mm). The water layer from the resulting two-phase mixture was decanted while still warm. The orange oil was crystallized from 65% ethanol-water to give a tan solid upon cooling to −10 degrees C. The solid was recrystallized from 50 mL of 65% ethanol-water. The off-white solid was washed with hot water (30 mL) to remove most of the remaining salicylic acid. The solid was recovered by filtration and was dried over 6 hours in a 50 degrees C. vacuum oven. The N-(3-methylsalicyloyl)-8-aminocaprylic acid was isolated as a light tan solid (12.32 g, 41%).

EXAMPLE 3

Preparation of N-(4-methylsalicyloyl)-8-aminocaprylic acid

A. Preparation of Oligo(4-methylsalicylate)

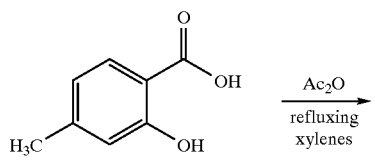

-continued

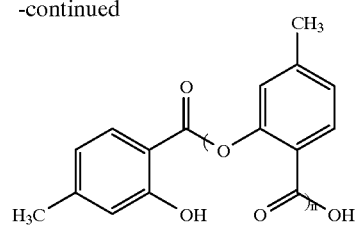

Acetic anhydride (14.60 mL, 15.80 g, 0.155 mol, 1.04 eq), 4-methylsalicylic acid (22.68 g, 0.149 mmol, 1.00 eq) and xylenes (90 mL) were added to a 250 mL, three-neck flask fitted with a magnetic stir bar, a thermometer, and a Dean-Stark trap with condenser. The flask was placed in a sand bath and heating of the cloudy white mixture was begun. The reaction mixture cleared to a yellow solution around 90° C. Most of the volatile organics (xylenes and acetic acid) were distilled into the Dean-Stark trap over three hours (135–146 degrees C.). Distillation was continued for another hour (a total of 110 mL distilled), during which the pot temperature slowly rose to 183 degrees C. and the distillate slowed to a trickle. The residue was poured off while still hot into an aluminum tray. Upon cooling a brittle yellow glass formed. The solid was ground to a fine powder. The 20.65 g of oligo(4-methylsalicylate) received was used without further purification.

B. Preparation of Salicyloylamino acid

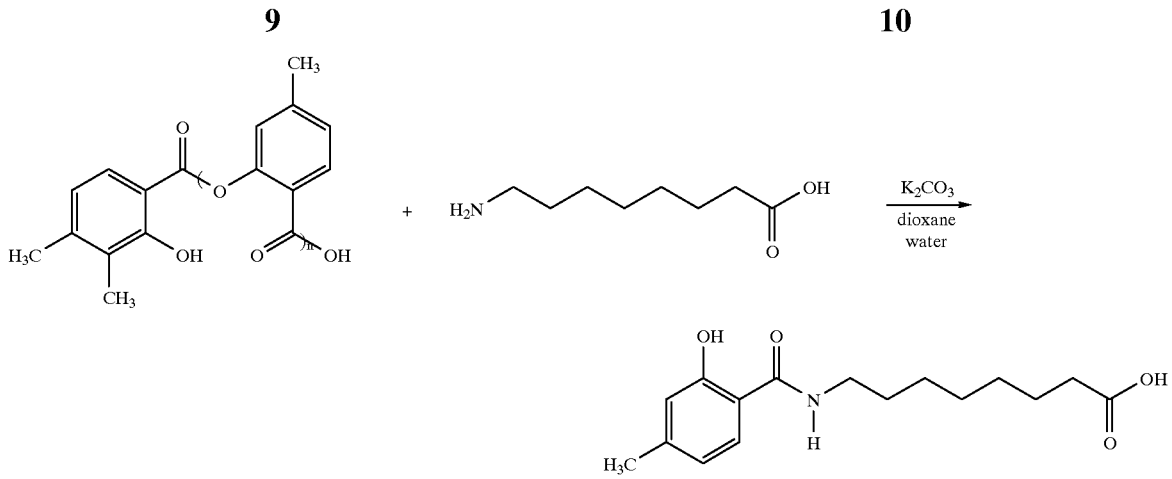

A 50% (by weight) solution of potassium carbonate (30 mL, 44.6 g, 0.161 mol, 1.19 eq), 8-aminocaprylic acid (21.43 g, 0.135 mol, 1.00 eq), and water (20 mL) were added to a 250 mL round bottom flask equipped with a magnetic stir bar and an addition funnel. The white cloudy mixture was treated with a solution of oligo(4-methylsalicylate) (20.65 g, 0.152 mmol 1.13 eq) and dioxane (80 mL), added over five minutes. The addition funnel was replaced with a condenser, and the reaction mixture was heated to 90 degrees C. for 4 hours (at which time the reaction was determined to have finished, by HPLC). The clear orange reaction mixture was cooled to 30 degrees C. and acidified to pH=1 with 3% (by vol) aqueous hydrochloric acid. All of the dioxane and some of the water were stripped (600 C, 50 mm). The solid (which precipitated from solution during stripping) was isolated by filtration while still warm. The light pink solid was recrystallized from 80 mL of 65% ethanol-water. The solid was recovered by filtration and was dried over 18 hours in a 50 degree C. vacuum oven. The N-(4-methylsalicyloyl)-8-aminocaprylic acid was isolated as a white solid (20.40 g, 52%).

EXAMPLE 4

Preparation of 3-(4-(3,5-dichlorosalicyloyl) aminophenyl)propionic acid

A. Preparation of Oligo(3,5-dichlorosalicylate)

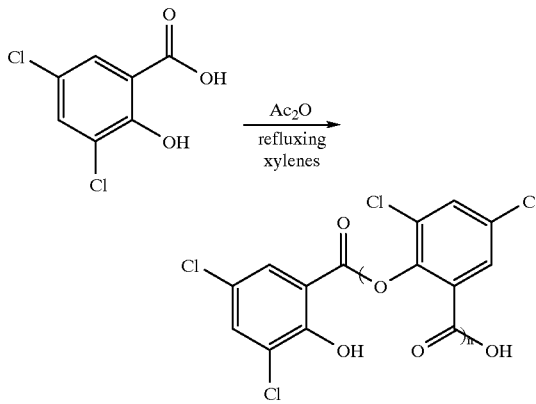

3,5-dichlorosalicylic acid (15.00 g, 0.073 mol, 1.0 equiv), acetic anhydride (7.69 g, 0.075 mol, 1.04 equiv), and xylenes (40 mL) were added to a 100 mL, three neck flask fitted with an argon purge, a magnetic stir bar, a thermometer, a Dean-Stark trap, and a cold water condenser. The flask was placed into a sand bath, and heating of the cloudy, off white reaction mixture was started. At 115° C. the reaction mixture cleared and a xylene/acetic acid mixture began to distill into the Dean-Stark trap at around 130–135 degrees C. Heating continued until most of the xylenes had distilled (approximately 40 mL of liquid was collected) and the reaction mixture thickened and became opaque brown in appearance. At this point, the temperature of the reaction mixture was 175 degrees C., and heating was stopped. The reaction mixture was allowed to cool to room temperature and a tan solid was isolated. The tan solid dried under vacuum for several days to give 15.3 g of oligo(3,5-dichlorosalicylate). 12.00 g of this material was carried on to the next step.

B. Preparation of Salicyloylamino acid

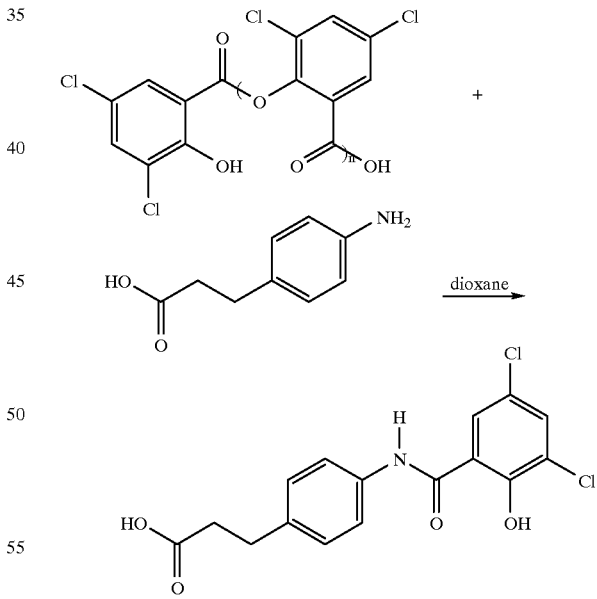

Oligo(3,5-dichlorosalicylate) (12.00 g, 0.070 mol, 1.10 equiv), 3-(4-aminophenyl) propionic acid (9.42 g, 0.057 mol, 1.0 equiv) and dioxane (150 mL) were added to a 500 mL round bottomed flask fitted with a magnetic stir bar, an argon purge, and a cold water condenser. A tan slurry was formed, and heating was started. The reaction mixture was heated at reflux for 3.5 hr. before being allowed to cool to room temperature. Dioxane was removed under vacuum leaving a brown residue. The brown residue was taken up in aqueous sodium hydroxide (2M, 200 mL). This mixture was filtered, extracted with ethyl acetate (350 mL), and acidified with 2N hydrochloric acid solution. A tan solid precipitated and was isolated by filtration. The tan solid was heated to boiling in a solution of ethanol (100 mL) and water (100 mL). Ethanol was then added to the boiling mixture until a clear solution was obtained. Activated charcoal was added, and the mixture was filtered. Upon cooling a white solid precipitated and was isolated by filtration. The white solid was dried overnight in a vacuum oven at 50 degrees C. The dried 3-(4-(3,5dichlorosalicyloyl)aminophenyl)propionic acid was isolated as a white solid (9.30 g, 46.0%); mp>225 degrees C.; 'H NMR (DMSO-d6) 612.9 (s, IH), 10.6 (s, IH), 8.15 (d, IH), 7.8 (d, 1H), 7.8 (d, 1H), 7.6 (d, 2H), 7.25 (d, 2H), 2.8 (t, 2H), 2.6 (t, 2H). Anal. Calcd for C16H13C12NO4: C, 54.24; H, 3.67; N, 3.95. Found: C, 54.21; H, 3.68; N, 3.89.

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

We claim:

1. A method for preparing a salicyloylamino acid, said method comprising:

(A) reacting an oligosalicylate and an amino acid to yield said salicyloylamino acid.

2. A method as defined in claim 1, wherein said oligosalicylate has the formula:

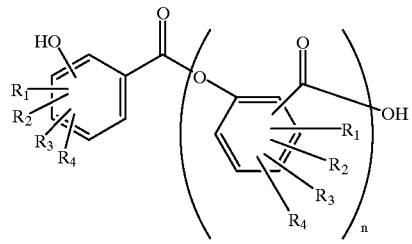

wherein $R_1$, $R_2$, $R_3$ and $R_4$ are independently hydrogen, fluorine, chlorine, bromine, iodine, $C_{1-9}$ linear or branched chain alkyl, $C_{1-9}$ linear or branched chain alkoxy, $C_{6-14}$ aryl, $C_{6-14}$ aryloxy or ($C_{6-14}$ aryl)($C_{1-9}$ linear or branched chain alkyl); and wherein n is an integer from about 1 to about 10.

3. A method as defined in claim 2, wherein said oligosalicylate has the formula:

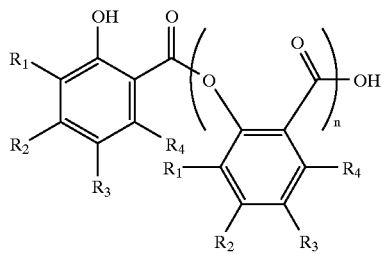

wherein $R_1$, $R_2$, $R_3$ and $R_4$ are independently hydrogen, fluorine, chlorine, bromine, iodine, $C_{1-9}$ linear or branched chain alkyl, $C_{1-9}$ linear or branched chain alkoxy, $C_{6-14}$ aryl, $C_{6-14}$ aryloxy or ($C_{6-14}$ aryl)($C_{1-9}$ linear or branched chain alkyl); and wherein n is an integer from about 1 to about 10.

4. A method as defined in claim 2, wherein said oligosalicylate has the formula:

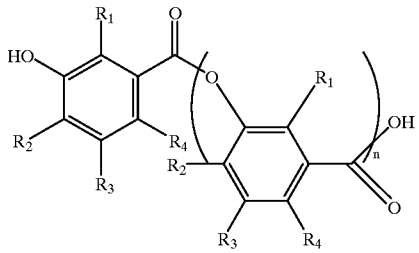

wherein $R_1$, $R_2$, $R_3$ and $R_4$ are independently hydrogen, fluorine, chlorine, bromine, iodine, $C_{1-9}$ linear or branched chain alkyl, $C_{1-9}$ linear or branched chain alkoxy, $C_{6-14}$ aryl, $C_{6-14}$ aryloxy or ($C_{6-14}$ aryl)($C_{1-9}$ linear or branched chain alkyl and wherein n is an integer from about 1 to about 10.

5. A method as defined in claim 2, wherein said oligosalicylate has the formula:

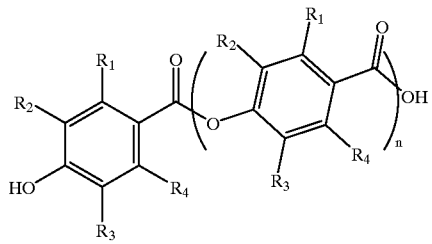

wherein $R_1$, $R_2$, $R_3$ and $R_4$ are independently hydrogen, fluorine, chlorine, bromine, iodine, $C_{1-9}$ linear or branched chain alkyl, $C_{1-9}$ linear or branched chain alkoxy, $C_{6-14}$ aryl, $C_{6-14}$ aryloxy or ($C_{6-14}$ aryl)($C_{1-9}$ linear or branched chain alkyl and wherein n is an integer from about 1 to about 10.

6. A method as defined in claim 2, wherein said oligosalicyloyl is selected from the group consisting of oligosalicylate, oligo-methyl salicylate, and oligo-dichlorosalicylate.

7. A method as defined in claim 1, wherein said amino acid is selected from the group consisting of natural amino acids and non-natural amino acids.

8. A method as defined in claim 7, wherein said amino acid has the formula:

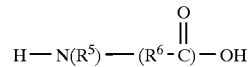

wherein $R^5$ is hydrogen, $C_1$–$C_4$ alkyl, or $C_2$–$C_4$ alkyl, or $C_2$–$C_4$ alkenyl;

$R^6$ is $C_1$–$C_{24}$ alkyl, $C_2$–$C_{24}$ alkenyl, $C_3$–$C_{10}$ cycloalkyl, phenyl, naphthyl, ($C_1$–$C_{10}$ alkyl) phenyl, (C2-$C_{10}$ alkenyl) phenyl ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl), or naphthyl ($C_2$–$C_{10}$ alkyl) or naphthyl ($C_2$–$C_{10}$ alkenyl);

$R^6$ being optionally substituted with $C_1$–$C_4$ alkyl, $C_2$–$C_4$ alkyenyl, $C_1$–$C_4$ alkoxy, —OH, —SH, —$CO_2R^7$, $C_3$–$C_{10}$ cycloalkyl, $C_3$–$C_{10}$ cycloalkenyl, heterocycle having 3–10 ring atoms wherein the hetero atom is one or more of N, O, S, or any combination thereof, aryl, ($C_1$–$C_{10}$ alk)aryl, ar($C_1$–$C_{10}$ alkyl) or any combination thereof;

$R^6$ being optionally interrupted by oxygen, nitrogen, sulfur, or any combination thereof; and $R^7$ is hydrogen, $C_1$–$C_4$ alkyl, or $C_2$–$C_4$ alkenyl.

9. A method as defined in claim 8, wherein said amino acid is selected from the group consisting of alanine, arginine, asparagine, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, phenylglycine, O-phosphoserine, β-alanine, α-amino butyric acid, γ-amino butyric acid, γ-(aminophenyl) butyric acid, α-amino isobutyric acid, citrulline, ε-amino caproic acid, 7-amino heptanoic acid, β-aspartic acid, aminobenzoic acid, aminocaprylic acid, aminophenyl acetic acid, aminophenyl butyric acid, γ-glutamic acid, cysteine (ACM), ε-lysine, ε-lysine (A-Fmoc), methionine sulfone, norleucine, norvaline, ornithine, d-ornithine, p-nitro-phenylalanine, hydroxy proline, 1,2,3,4,-tetrahydroisoquinoline-3-carboxylic acid, aminodecanoic acid, and thioproline.

10. A method as defined in claim 9, wherein said amino acid is aminocaprylic acid.

11. A method as defined in claim 2, wherein said oligosalicylate is oligo-n-salicylate, said amino acid is aminocaprylic acid, and said salicyloylamino acid is N-(salicyloyl)-8-aminocaprylic acid.

12. A method as defined in claim 2, wherein said reacting is conducted in an aqueous medium.

13. A method as defined in claim 12, wherein said aqueous medium comprises water.

14. A method as defined in claim 13, wherein said aqueous medium further comprises sodium hydroxide.

15. A method as defined in claim 14, wherein said aqueous medium further comprises an organic solvent selected from the group consisting of dioxane, xylene, acetonitrile, tetrahydrofuran, and 1-methoxy-propanol.

16. A method as defined in claim 2, wherein said reacting occurs at a temperature ranging from about 25 to about 150° C.

17. A method as defined in claim 2, wherein the molar ratio of said oligosalicylate to said amino acid ranges from about 0.5 to about 2.0.

18. A method as defined in claim 2, wherein said reaction is allowed to take place for about 0.5 to about 24 hours.

19. A method as defined in claim 2, further comprising
(B) isolating said salicyloylamino acid.

20. A method as defined in claim 19, wherein said isolating comprises filtering.

21. A method as defined in claim 20, wherein said isolating further comprises drying.

* * * * *